(12) United States Patent
Dolle

(10) Patent No.: US 6,241,660 B1
(45) Date of Patent: Jun. 5, 2001

(54) CENTRAL NERVOUS SYSTEM SHUNT MONITORING SYSTEM

(76) Inventor: Stephen M. Dolle, 3908-1/2 River Ave., Newport Beach, CA (US) 92663

( * ) Notice: Subject to any disclaimer, the term of this patent is extended or adjusted under 35 U.S.C. 154(b) by 0 days.

(21) Appl. No.: 09/197,125

(22) Filed: Nov. 20, 1998

Related U.S. Application Data

(60) Provisional application No. 60/066,727, filed on Nov. 20, 1997.

(51) Int. Cl.$^7$ .................................................. A61B 5/00
(52) U.S. Cl. .............................. 600/300; 600/561; 604/8
(58) Field of Search .................... 609/8–10; 600/561, 600/300–301, 544–545; 128/920–925

(56) References Cited

U.S. PATENT DOCUMENTS

| | | | |
|---|---|---|---|
| 4,003,141 | * | 1/1977 | Le Roy . |
| 4,385,636 | * | 5/1983 | Cosman . |
| 4,593,703 | * | 6/1986 | Cosman . |
| 5,405,316 | * | 4/1995 | Magram ..................................... 604/8 |
| 5,795,307 | * | 8/1998 | Krueger ................................. 600/561 |

* cited by examiner

*Primary Examiner*—Cary O'Connor
*Assistant Examiner*—Michael Astorino
(74) *Attorney, Agent, or Firm*—Knobbe, Martens, Olson & Bear, LLP

(57) ABSTRACT

A method of monitoring Central Nervous Shunt performance by sampling non-invasive data from a patient with hydrocephalus condition. The sampled data is processed to produce a determination of probable shunt operation. Where the shunt may not operate properly, the processing produces a prediction of possible shunt malfunction. The processing includes a method to assess which of a set of possible malfunctions is the most likely. The processing can also be used to advise the user on how to remedy the problem diagnosed. The shunt performance rating can also be used to monitor shunt performance over time and process the time data to provide for a shunt operation status or observe the compatibility of a particular shunt type to a patient.

12 Claims, 11 Drawing Sheets

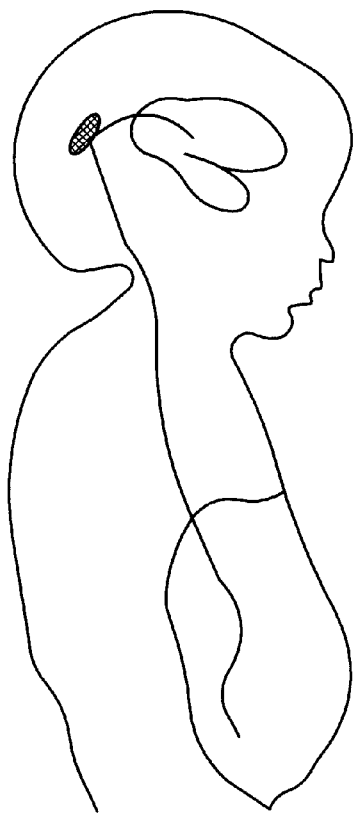
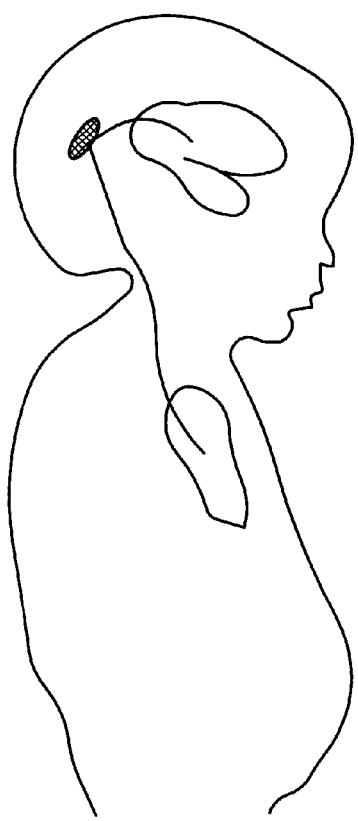
VP SHUNT
FIG.2B
VA SHUNT
FIG.2A

FIG. 3

MONITORING SYSTEM WORK PAGE

| TIME | ACTIVITY/EVENT | NAUSEA | HEADACHE | SHUNT TRACT | SHUNT RESERVOIR FINGER TEST | | | | COGNITIVE | POSITIONAL TEST | |
|---|---|---|---|---|---|---|---|---|---|---|---|
| | | | | | Proximal | Distal | In-Line | Refill | | Supine | Upright |
| 1. | ___ | 3 2 1 N | N 1 2 3 | ___ | -2 -1 N +1 +2 | -2 -1 N +1 +2 | -2 -1 N +1 +2 | -2 -1 N +1 +2 | -3 -2 -1 N | N ↓ NC ↑ | N ↓ NC ↑ |
| 2. | ___ | 3 2 1 N | N 1 2 3 | ___ | -2 -1 N +1 +2 | -1 -1 N +1 +2 | -2 -1 N +1 +2 | -2 -1 N +1 +2 | -3 -2 -1 N | N ↓ NC ↑ | N ↓ NC ↑ |
| 3. | ___ | 3 2 1 N | N 1 2 3 | ___ | -2 -1 N +1 +2 | -2 -1 N +1 +2 | -2 -1 N +1 +2 | -2 -1 N +1 +2 | -3 -2 -1 N | N ↓ NC ↑ | N ↓ NC ↑ |
| 4. | ___ | 3 2 1 N | N 1 2 3 | ___ | -2 -1 N +1 +2 | -2 -1 N +1 +2 | -2 -1 N +1 +2 | -2 -1 N +1 +2 | -3 -2 -1 N | N ↓ NC ↑ | N ↓ NC ↑ |
| 5. | ___ | 3 2 1 N | N 1 2 3 | ___ | -2 -1 N +1 +2 | -2 -1 N +1 +2 | -2 -1 N +1 +2 | -2 -1 N +1 +2 | -3 -2 -1 N | N ↓ NC ↑ | N ↓ NC ↑ |
| 6. | ___ | 3 2 1 N | N 1 2 3 | ___ | -2 -1 N +1 +2 | -2 -1 N +1 +2 | -2 -1 N +1 +2 | -2 -1 N +1 +2 | -3 -2 -1 N | N ↓ NC ↑ | N ↓ NC ↑ |
| 7. | ___ | 3 2 1 N | N 1 2 3 | ___ | -2 -1 N +1 +2 | -2 -1 N +1 +2 | -2 -1 N +1 +2 | -2 -1 N +1 +2 | -3 -2 -1 N | N ↓ NC ↑ | N ↓ NC ↑ |
| 8. | ___ | 3 2 1 N | N 1 2 3 | ___ | -2 -1 N +1 +2 | -2 -1 N +1 +2 | -2 -1 N +1 +2 | -2 -1 N +1 +2 | -3 -2 -1 N | N ↓ NC ↑ | N ↓ NC ↑ |
| 9. | ___ | 3 2 1 N | N 1 2 3 | ___ | -2 -1 N +1 +2 | -2 -1 N +1 +2 | -2 -1 N +1 +2 | -2 -1 N +1 +2 | -3 -2 -1 N | N ↓ NC ↑ | N ↓ NC ↑ |
| 10. | ___ | 3 2 1 N | N 1 2 3 | ___ | -2 -1 N +1 +2 | -2 -1 N +1 +2 | -2 -1 N +1 +2 | -2 -1 N +1 +2 | -3 -2 -1 N | N ↓ NC ↑ | N ↓ NC ↑ |

| POSITIONAL VALUE | ICP VALUE | RESERVOIR ANL. | SHUNT SYSTEM ANL. | DIACEPH DIAGNOSIS |
|---|---|---|---|---|
| 1. - + ±/N N | -3 -2 -1 N +1 +2 +3 | ___ | ___ | A B C D E F G H I J K L M |
| 2. - + ±/N N | -3 -2 -1 N +1 +2 +3 | ___ | ___ | A B C D E F G H I J K L M |
| 3. - + ±/N N | -3 -2 -1 N +1 +2 +3 | ___ | ___ | A B C D E F G H I J K L M |
| 4. - + ±/N N | -3 -2 -1 N +1 +2 +3 | ___ | ___ | A B C D E F G H I J K L M |
| 5. - + ±/N N | -3 -2 -1 N +1 +2 +3 | ___ | ___ | A B C D E F G H I J K L M |
| 6. - + ±/N N | -3 -2 -1 N +1 +2 +3 | ___ | ___ | A B C D E F G H I J K L M |
| 7. - + ±/N N | -3 -2 -1 N +1 +2 +3 | ___ | ___ | A B C D E F G H I J K L M |
| 8. - + ±/N N | -3 -2 -1 N +1 +2 +3 | ___ | ___ | A B C D E F G H I J K L M |
| 9. - + ±/N N | -3 -2 -1 N +1 +2 +3 | ___ | ___ | A B C D E F G H I J K L M |
| 10. - + ±/N N | -3 -2 -1 N +1 +2 +3 | ___ | ___ | A B C D E F G H I J K L M |

| INTERVENTION | STATUS | ADVANCED DIAGNOSIS |
|---|---|---|
| 1st. ___ | → NC ↑ | A B C D E F G H I J K L M |
| 2nd. ___ | → NC ↑ | A B C D E F G H I J K L M |
| 3rd. ___ | → NC ↑ | A B C D E F G H I J K L M |
| 4th. ___ | → NC ↑ | A B C D E F G H I J K L M |
| 5th. ___ | → NC ↑ | A B C D E F G H I J K L M |
| 1st. ___ | → NC ↑ | A B C D E F G H I J K L M |
| 2nd. ___ | → NC ↑ | A B C D E F G H I J K L M |
| 3rd. ___ | → NC ↑ | A B C D E F G H I J K L M |
| 4th. ___ | → NC ↑ | A B C D E F G H I J K L M |
| 5th. ___ | → NC ↑ | A B C D E F G H I J K L M |

INTERVENTIONS (IV'S)
1. Lay Down and Rest
2. Lay Down to Trendelenburg
3. Exercise Activities/Strain
4. Pinch Off Valve Occluder
5. Close Off ASD/SCD Mechanism
6. Assume Upright Posture
7. Flush Shunt Distally/Purge
8. Life Up Overlying Scalp
9. Flush Shunt Proximally
10. Manipulate Abd./Shunt Tract

SHUNT MALFUNCTIONS BY TYPE (LETTER)
A. Proximal Catheter/Valve Obstruction
B. Proximal Obstruction w/Collapsed Vent.
C. Proximal Disconnect of Components
D. Infection w/Proximal Valve Obstruction
E. NORMAL System Function
F. NORMAL Function w/ CSF Underdrainage
G. Shunt Overdrainage/Hypotension (incl. ASDs)
H. ASD Shunt Overfunction w/ Underdrainage
I. Distal Catheter/Valve Obstruction
J. Mal-Positioned Distal Catheter
K. Distal Disconnect of Components
L. Infection w/Distal Obstruction
M. Other Pathology/Seizure Activity

DATE: ___
PATIENT: ___
PHYSICIAN: ___
SHUNT TYPE: ___
SPECIAL INSTR ___

FIG.5

SLIDE CHART PROCESSOR

TEMPLATE ONE

Instructions:

1. Match the results of the Positional Test to the Key Column at left. Circle the corresponding Positionval Value. Record this on Work Page. Go to Step 2.

2. In Window (A), set Cognitive Score at Headache Score. Read ICP Value in Window B, C, D, or E by matching Positional Value to Nausea Score. Record. Results get ploted on Day-Chart. Go to Step 3.

Step 1. Positional Value Key:

| | Supine | Upright | Positional Value |
|---|---|---|---|
| 1. | N → NC ↑ | N → NC ↑ | = − |
| 2. | N → NC ↑ | N → NC ↑ | = − |
| 3. | N → NC ↑ | N → NC ↑ | = + |
| 4. | N → NC ↑ | N → NC ↑ | = + |
| 5. | N → NC ↑ | N → NC ↑ | = ± N |
| 6. | N → NC ↑ | N → NC ↑ | = N (normal) |

Step 2. Determining ICP Value:

| Headache (HA) | | | | Window |
|---|---|---|---|---|
| Cognitive | N | 1 | 2 | 3 |
| | −3 | −2 | −1 | N | (A) |

| Positional Value = + | ↓ | 3 | 1 | 1 | N |
| | +2 (ICP) | +1 | +1 | N | ↑ | (B) |

| Positional Value = ± N | ↓ | 3 | 1 | 1 | N |
| | +2 (ICP) | ±1 | 1 | N | ↑ | (C) |

Nausea

| Positional Value = N | ↓ | 3 | 1 | 1 | N |
| | +2 (ICP) | +1 | 1 | N | ↑ | (D) |

Nausea

| Positional Value = − | ↓ | 3 | 1 | 1 | N |
| | −2 (ICP) | −1 | 1 | N | ↑ | (E) |

TEMPLATE TWO

Steps 3, 4, 5. Shunt System Analysis:

|  | -2 | -1 | N | +1 | +2 |  |
|---|---|---|---|---|---|---|
| Proximal (And In-Line) |  |  |  |  | +2 | Window (F) |
| Distal (And Refill) | -2 |  |  |  |  | Window (F) |

Reservoir Analysis

Refill Value

| +2 | HI |
|---|---|
| +1 | HIJK |
| N | FHJK |
| -1 | AIJK |
| -2 | AJ |
| In-line | . |

Window (G)

Shunt System Analysis

Reservoir Malfunctions Group  | AIJK |  Window (H)

| Shunt Tract |  |
|---|---|
| No Pain/No Swelling | IK |
| Proximal Pain/Swelling | AI |
| Proximal Pain/No Swelling | AI |
| Proximal Swelling/No Pain | I |
| Distal Pain/Swelling | JK |
| Distal Pain/No Swelling | JK |
| Distal Swelling/No Pain | K |

Window (I)

Instructions:

3. In Window F, set Distal Score at Proximal Score. Go to Step 4

4. In Window G, and without moving the slide, select the malfunction(s) letter group that corresponds with the patient's Refill Score, shaded in the Orange Box. Record it. For In-Line Reservoir types, Record the malfunction(s) that appear next to In-Line (Orange Box). Go to Step 5.

5. Set Window H to the malfunction(s) group identified in Step 4, and read the Shunt System Analysis result in Window I next to Shunt Tract finding (Orange Box). Record. Go to Step 6.

Shunt Malfunctions by Type (Letter Key):

A. Proximal Catheter/Valve Obstruction
B. Proximal Obstruction w/Collapsed Vent.
C. Proximal Disconnect of Components
D. Infection w/ Proximal/Valve Obstruction
E. NORMAL System Function
F. NORMAL Function w/ CSF Underdrainage
G. Shunt Overdrainage/Hypotension (inc. ASDs)
H. ASD Shunt Overfunction w/ Underdrainage
I. Distal Catheter/Valve Obstruction
J. Mal-Positioned Distal Catheter
K. Distal Disconnect of Components
L. Infection w/ Distal Obstruction
M. Other Pathology/Seizure Activity

TEMPLATE THREE

Steps 6, 7, 8, 9.  Patient/Shunt System Diagnosis:

Shunt System Analysis + Groups

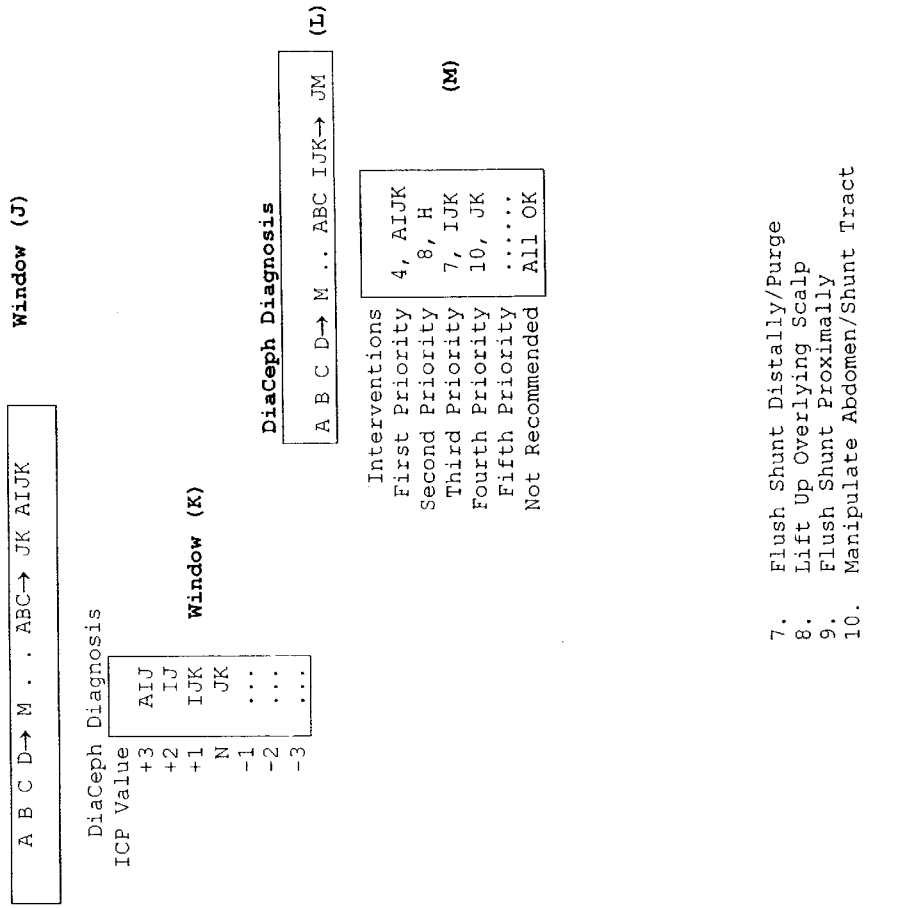

Instructions:

6. In Window J, set slide to Shunt System Analysis result obtained in Step 5. Now Go to Step 7.

7. In Window K, and without moving the slide, select the malfunction(s) letter group that corresponds to the ICP Value (from Step 2) shaded in the Orange Box, and Record it. This Code(s) represents the diagnosis in the Standard DiaCeph Test. To continue with Interventions, Go to Step 8.

8. In Window L, set slide to the Diagnosis obtained in Step 7. Without moving the slide, Read the Interventions in order of priority in Window M. Record these. Go to Step 9.

9. Do one Intervention at a time. Record the Status. Go to Step 10.

Interventions (No. Key):

1. Lay Down and Rest
2. Lay Down in Trendelenburg
3. Exercise Activities/Strain
4. Pinch off Valve Occluder
5. Close Off ASD/SCD Mechanism
6. Assume Upright Posture
7. Flush Shunt Distally/Purge
8. Lift Up Overlying Scalp
9. Flush Shunt Proximally
10. Manipulate Abdomen/Shunt Tract

TEMPLATE FOUR
Interventions

```
| 1  | 2  | 3  | 4  | 5  | 6  | 7  | 8  | 9  | 10 |
| NC | NC | NC | NC | NC | NC | NC | NC | NC | NC |
→  ↑  →  ↑  →  ↑  →  ↑  →  ↑  →  ↑  →  ↑  →  ↑  →  ↑  →  ↑
```

Window (N)

Steps 10 and 11. Using Interventions:

Shunt Malfunctions

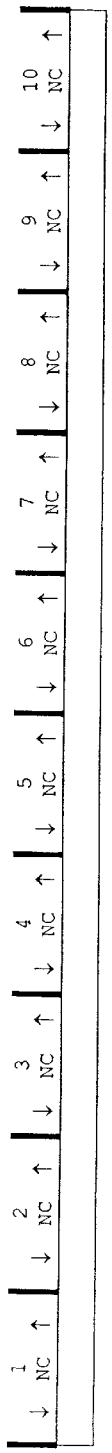

| | Window (O) |
|---|---|
| A. Proximal Catheter/Valve Obstruction | % |
| B. Proximal Obstruction w/ Collapsed Vent. | % |
| C. Proximal Disconnect of Components | nr |
| D. Infection w/ Proximal Valve Obstruction | nr |
| E. NORMAL System Function | % |
| F. NORMAL Function w/ CSF Underdrainage | F — |
| G. Shunt Overdrainage/Hypotension (incl. ASD) | % |
| H. ASD Shunt Overfunction w/ Underdrainage | H |
| I. Distal Catheter/Valve Obstruction | I |
| J. Mal-Positioned Distal Catheter | J |
| K. Distal Disconnect of Components | K |
| L. Infection w/ Distal Obstruction | L — |
| M. Other Pathology/Seizure Activity | | nr: denotes Not Recommended

Instructions:

10. In Window N, set slide indicator arrow at ↓, NC, or ↑, for Status result of the Intervention being performed. Go to Step 11.

11. In Window O, and without moving the slide, read the Malfunction Code that appears in the Window on the same line(s) as the Malfunction(s) being investigated. Record on Work Page. Go back to Step 9 and perform the remaining interventions, to r/o other Diagnosis(s).

Interventions (No. Key):

1. Lay Down and Rest
2. Lay Down in Trendelenburg
3. Exercise Activities/Strain
4. Pinch off Valve Occluder
5. Close Off ASD/SCD Mechanism
6. Assume Upright Posture
7. Flush Shunt Distally/Purge
8. Lift Up Overlying Scalp
9. Flush Shunt Proximally
10. Manipulate Abdomen/Shunt Tract

*FIG.8*

TYPE 1: SHUNT WITH CENTRAL RESERVOIR, PROXIMAL AND DISTAL OCCLUDERS.

TYPE 2: SHUNT WITH IN-LINE RESERVOIR, NO DIRECTIONAL OCCLUDERS.

CENTRAL NERVOUS SYSTEM SHUNT MONITORING SYSTEM

This application claims benefit to Provisional Application 60/066,727 filed Nov. 20, 1997.

FIELD OF THE INVENTION

This invention relates to a system for monitoring a shunt performance for patients with a hydrocephalus condition.

BACKGROUND OF THE INVENTION

Hydrocephalus comes from the Greek: hydro means water, cephalus means head. Hydrocephalus is an abnormal accumulation of fluid—cerebrospinal fluid ("CSF") within cavities called ventricles, inside the brain. CSF is produced in the ventricles, circulates through the ventricular system, and is absorbed into the bloodstream. CSF is reabsorbed at a rate that is dependent on regulation of intracranial pressure ("ICP"). CSF is in constant circulation and has many important functions. It surrounds the brain and spinal cord and acts as a protective cushion against injury. CSF contains nutrients and proteins that are needed for the nourishment and normal function of the brain. It also carries waste products away from surrounding tissues. Hydrocephalus occurs when there is an imbalance between the amount of CSF that is produced and the rate at which it is absorbed. As the CSF builds up, it causes the ventricles to enlarge and the pressure inside the head to increase. Congenital Hydrocephalus is thought to be caused by a complex interaction of genetic and environmental factors. Aqueductal stenosis, an obstruction of the cerebral aqueduct, is the most frequent cause of congenital hydrocephalus. Acquired hydrocephalus may result from spina bifida, intraventricular hemorrhage, meningitis, head trauma, tumors and cysts. Hydrocephalus affects about one in every 500 children born.

There is no known way to prevent or cure hydrocephalus. To date, the most effective treatment is surgical insertion of a shunt. A shunt is a flexible tube placed into the ventricular system of the brain which diverts the flow of CSF into another region of the body, most often the abdominal cavity or a chamber of the heart, where it can be absorbed. A valve within the shunt attempts to maintain the CSF at a pre-estimated ICP by allowing the valve to open in response to that pressure level. Under most circumstances, no specific testing is performed in advance of surgery to try and estimate the patient's flow needs. Since the flow needs are not determined prior to the insertion of the shunt, more surgery may be necessary in the future to fit a matching valve for the patient.

A shunt is simply a drain, which diverts the accumulated CSF from the obstructed pathways and returns it to the bloodstream. The device consists of a system of tubes with a valve to control the rate of drainage and prevent back-flow. It is inserted surgically so that the upper end is in a ventricle of the brain and the lower end leads either into the heart (ventriculo-atrial, FIG. 2A) or into the abdomen (ventriculo-peritoneal, FIG. 2B). The device is completely enclosed so that all of it is inside the body. Other drainage sites such as the outer lining of the lungs (ventriculo-pleural shunt) can also be used. In most cases, the shunts are intended to stay in place for life, although alterations or revisions might become necessary from time to time.

Today, there are numerous types of shunts but while different in appearance they work in a very similar manner. None can be said to be significantly better or worse than others, and the shunt is usually chosen by the surgeon based on experience, cost and personal preference. Special in-hospital 24-hour monitoring can be utilized to evaluate the degree of shunt dependency and ICP requirements. The hospital monitoring is expensive, complicated, and is usually only a last resort effort when the patient condition is quite severe.

Originally, shunts were inserted so that a tube drained CSF from the ventricles in the brain, through the valve and through another tube into a vein in the neck and then into the heart (FIG. 2A). While these are still used, most currently drain the CSF into the abdomen (FIG. 2B) and the bottom tube can be felt over the ribs. Despite all these developments, shunting can have complications. These can be divided into under-drainage, over-drainage and infection. The treatment involves operations, often indeterminate hospital stays and disappointing relapses before a successful outcome could eventually be realized. There is a need for a way to monitor hydrocephalus patients during their daily routines after having a shunt implantation as to better evaluate the performance of the shunt and valve matching for the patient.

SUMMARY OF THE INVENTION

In accordance with the invention there is provided a Central Nervous System ("CNS") Shunt Monitoring System, referred to as "DiaCeph™ Test," which is a home and physician office monitoring system for hydrocephalus patients with CNS shunts. The DiaCeph™ Test evaluates specific neurological findings of the hydrocephalus patient, processes it with a special unit, introduces specifically tailored interventions, and results in a specific diagnosis. The system provides for a standardization for communicating the performance of a shunt. While in the past patients struggled to communicate the symptoms they are experiencing to a doctor, with the DiaCeph™ monitoring system, the communication is effortless. The system can either directly communicate with a doctor's computer or generate a printout of the observations for a doctor to review.

The DiaCeph™ Shunt Monitoring System can be described in four parts. First, the user evaluates and scores real-time sets of patient data. Next, the data is processed in the DiaCeph™ processor. The processor carries out a series of steps and calculations whereby the patient's data is analyzed and coded. It employs proprietary calculations as it considers the possible shunt scenarios, and renders a specific diagnosis from a list of shunt malfunctions. Next, the patient's data is plotted on a chart. The chart serves as a means for monitoring "live" patient data over the course of time. This is compared to the patient's pre-established normal, and to a DiaCeph™ Standard. The final part is the Advanced DiaCeph™ Test. Here specific non-invasive Interventions or manipulations are used to explore a complex diagnosis. The Slide Chart or processor chooses the Interventions, any to avoid, and confirms or rejects the diagnosis. These Interventions also help manage many common hydrocephalus complaints.

The DiaCeph™ Test will assist the physician in determining if a patient is experiencing a malfunction necessitating costly hospital care and testing, a matter of importance in today's insurance market. It will serve families with the benefits of a proven test product for evaluating complaints in the home. It could become a standard in hydrocephalus research.

Routine use of the DiaCeph™ Test will reduce exploratory testing and dependence on emergency room treatment, and provide the shunted patient and his/her family with increased independence in the home setting. The ability to track real time shunt performance will no doubt lead to improved care and treatment.

BRIEF DESCRIPTION OF THE DRAWINGS

FIG. 2A is an illustration of a Ventriculo-Atrial shunt;

FIG. 2B is an illustration of a Ventriculo-Peritoneal shunt;

FIG. 3 is an example of the DiaCeph™ monitoring work page used to collect data concerning a patient;

FIG. 5 is an example of a first template of the DiaCeph™ processor;

FIG. 6 is an example of a second template of the DiaCeph™ processor;

FIG. 7 is an example of a third template of the DiaCeph™ processor;

FIG. 8 is an example of a fourth template, including interventions, of the DiaCeph™ processor;

DETAILED DESCRIPTION OF THE PREFERRED EMBODIMENT

Figure 1A:
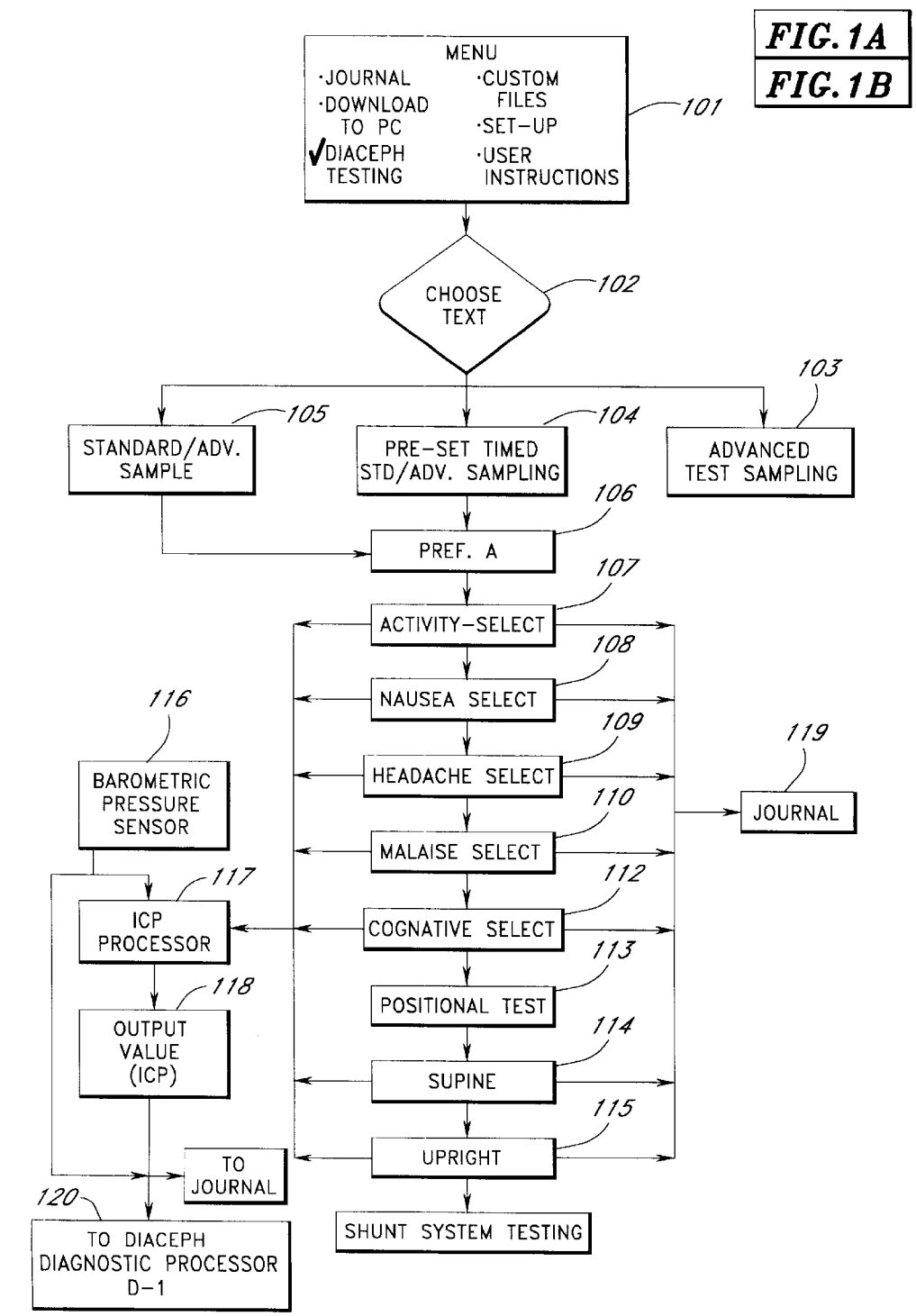
FIG. 1A is a flowchart illustrating the operation of some part of the DiaCeph™ system.

With reference to FIG. 1, the steps taken by a system in accordance with the method of the present invention will be illustrated. First, the user selects options from a start menu 101. Some of the options that can be available are a journal review, download data to PC, conduct tests, set-up preferences, review user instructions, or create custom files. The user should select a shunt type from the list of shunt types available. The user can also select a test profile to conduct other than the default profile. The test preference will usually be recommended by a doctor or other treating party. The user may also select a desired cognitive test at this time such that the same cognitive test is performed each time a sample data is taken.

Once all the information concerning the patient is entered, the system will either prompt the user to conduct the specific test or direct the user to a list of tests to perform that is applicable to the information entered. Once the user selects the "conduct tests" entry the system prompts the user to choose a test type 102 from a standard or advance single sample test 105, a pre-set timed standard 104 or advance sampling 103 (a set of samples over a predefined time period). The standard sampling will proceed in accordance with a pre-selected preference test profile. In the example shown preference A 106 was selected. The preference includes an activity 107, nausea 108, Headache 109, malaise 110, and cognitive scoring 112. Additionally the preference includes both positional tests 113, the supine 114, and upright 115 positions. All data from the scoring and positional tests is transferred to both the journal 119 and the ICP processor 117. The journal 119 is used to store the observations for later review or processing. The ICP processor 117 in the example shown, uses a barometric pressure sensor 116 in estimating the ICP. The processor 117 then sends the ICP to the output unit 118. The output unit 118 transmits the ICP to the diagnostic processor 120.

Figure 1B:
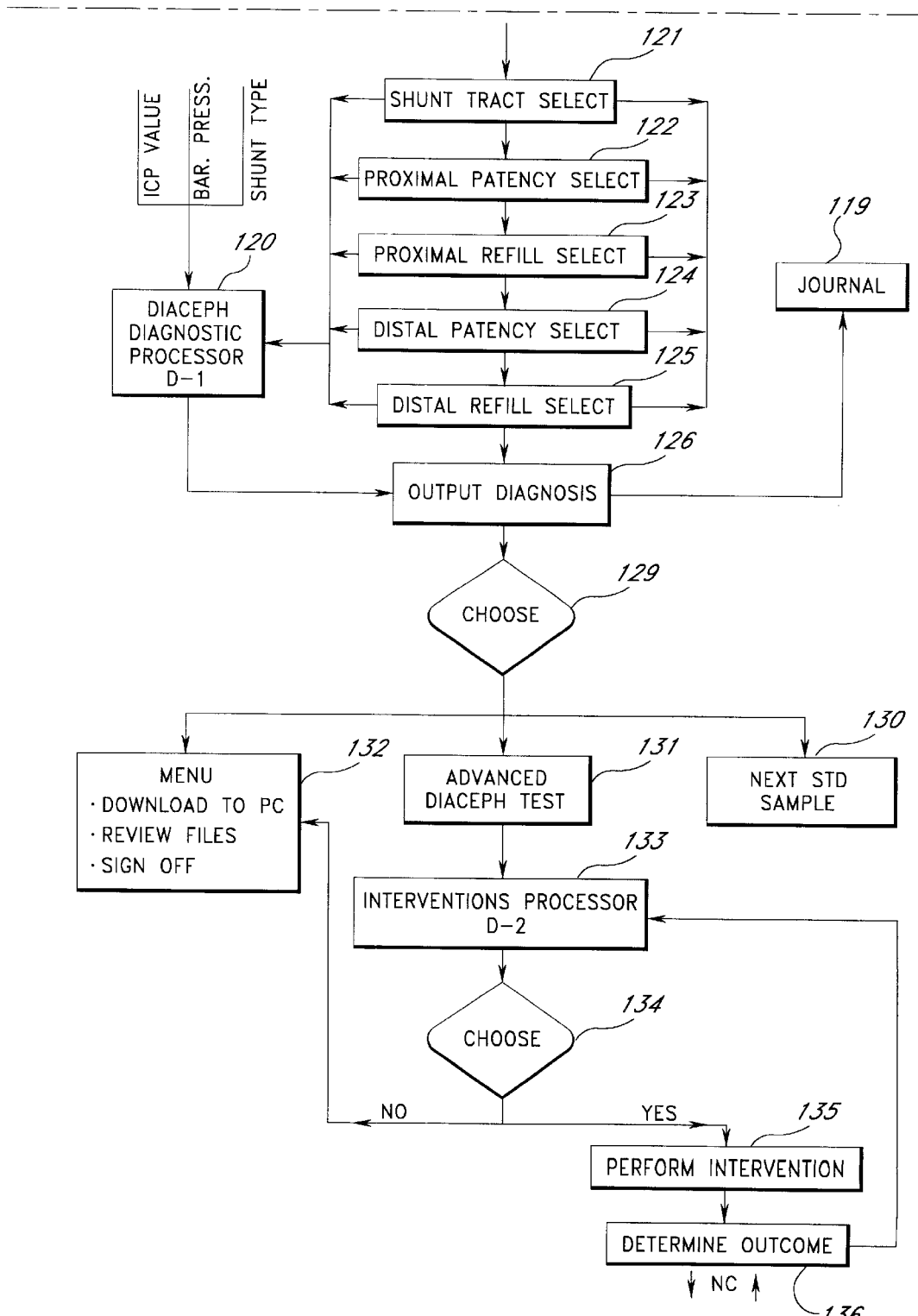
FIG. 1B is a flowchart illustrating the operation of parts of the DiaCeph™ system following those in FIG. 1A.

In FIG. 1B, the steps following those in FIG. 1A are illustrated. The next sample is that of the shunt tract 121. The observation of the shunt tract 121 is followed by a proximal patency 122, proximal refill 123, distal patency 124, and distal refill 125 observations. The observation data is transmitted to the journal 119 and the diagnostic processor 120. The diagnostic processor 120 uses the observations, barometric pressure data, and shunt type information to generate a diagnosis 126.

Once a diagnosis is generated the user can choose whether to end the test and return to the menu 101, perform the advanced portion of the test 131, or take another sample 130. The advanced portion of the test 131 will take the user to the intervention processor 133 which will generate a set of interventions to perform. If there are interventions to perform, the answer in step 134 will be yes. The user will then perform the intervention 135 and determine its outcome 136. The outcome is passed back to the intervention processor 133 for further analysis. Once all recommended interventions are performed the user will be prompted back to the menu 101. A computerized unit that prompts the user to conduct tests and enter results can greatly simplify the data entry procedure. The description below includes the details of some of the steps in FIGS. 1A and 1B with reference to the later Figures.

Step 1. Time and Nausea Measurements. Write down the time of day next to the sample under "Time" on the work page of FIG. 3. List any activity or medical event that preceded the hydrocephalus incident being investigated under "Activity/Event." It might be a fever, headache or stare-like state upon awakening, or difficulty following an activity. Next, identify any Nausea or Vomiting by circling a representative score under "Nausea." Scoring: 3=severe vomiting and nausea; 2=moderate nausea with some vomiting; 1=nausea only, may warrant medication or intervention.

Step 2. Identifying the Headache (HA). Identify the patient's headache as the worst degree of severity that was associated with the hydrocephalus incident in this test. If necessary, place the patient in the incident position for several minutes. Circle the headache score that best corresponds to its severity under "Headache." Scoring: N=normal, no HA; 1=moderate HA, but tolerable, may or may not medicate, often able to continue activities; 2=moderately severe HA, requires medication, often requires lying down, no activity, may include nausea or vomiting; 3=severe HA, requires strong medication, stop all activities, rest, likely vomiting.

A "malaise" score (not on chart in FIG. 3, but mentioned in the flow chart of FIG. 1) may be prompted under certain test preferences. Malaise can be best described as a debilitating feeling regarding stamina and health, often shown as weakness. The user should identify the score that best describes the conditions. The possible scores can be, for example, N=normal; 1=moderate, but tolerable feeling of weakness, may affect but not prevent activities; 2=moderately severe level where many common activities are not possible; 3=severe, bed ridden and confined.

Step 3. The Shunt/Reservoir Evaluation. The first portion of this test involves a physical examination of the shunt valve and catheter tract. Start where the ventricular catheter exits the skull. Check the shunt valve, connectors, and distal catheter by running your fingers along the patient's shunt tract. Look for signs of fluid accumulation and focal pain. If necessary, have the patient hold their breath as you inspect the chest and abdomen. If unsure of the findings, mark "No Pain/No Swelling" followed by a "?". Identify findings under the Shunt Tract column of FIG. 3 as: No Pain/No Swelling (No P/S), Proximal Pain/Swelling (Prox. P/S), Proximal Pain/No Swelling, No Pain/Proximal Swelling, Distal Pain/Swelling, Distal Pain/No Swelling, No Pain/Distal Swelling. Abbreviate when needed.

The DiaCeph™ system provides, for example, two separate test methods for performing the Shunt Reservoir Finger Test. The two methods correspond to two types of CNS shunt systems incorporating reservoirs, referred to here as Type 1 and Type 2 shunts. A selection of shunt type at the start of the sampling procedure will direct the user to the proper test to perform for the selected shunt type.

Figure 10:
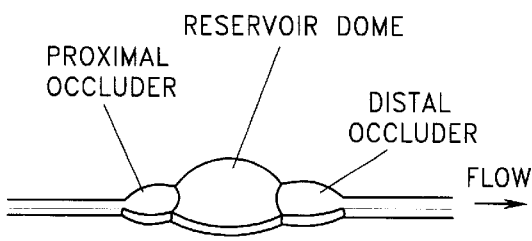
FIG. 10 is an illustration of a shunt valve with a reservoir, proximal, and distal occluders.
Figure 12:
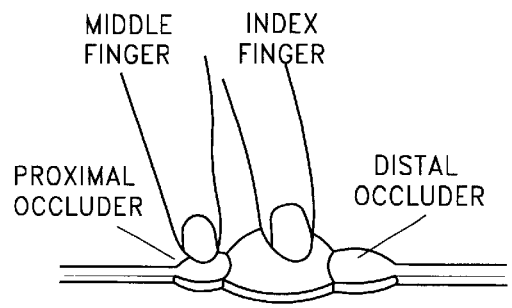
FIG. 12 is an illustration of the distal patency check testing procedure for the shunt of FIG. 10.
Figure 11:
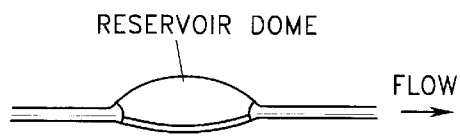
FIG. 11 is an illustration of a shunt reservoir with no directional occluders.

Type 1 shunt systems (FIG. 10) consist of a differential pressure shunt valve with an integral central reservoir and proximal and distal directional occluders on each side of the valve. The system terms its reservoir test method for this shunt as Method 1 (FIGS. 10/12). Type 2 shunt systems (FIG. 11) employ an In-Line reservoir without the occluders, and hence are not capable of selective flushing. The applicable test technique is termed Method 2 (FIGS. 11/13). It may be applied to any CNS shunt that has a Percutaneous flushing reservoir. It is important to verify the type of reservoir/shunt system so as to obtain the most reliable data possible from this test.

The DiaCeph™ method provides a sampling technique for Type 1 systems, termed the "Two Finger Palpating Technique." This technique employs the index/middle fingers of the same hand to depress and sample the reservoir. Other users may prefer to use the index or middle fingers of both hands to depress and sample the reservoir. The best technique for any given user is one that is comfortable to the user and can be replicated in a reliable manner. Reservoir testing is best performed in the Supine posture, as test results vary slightly with posture.

Two Finger Palpating Technique (FIGS. 10/12):

Face the patient with your fingers over the shunt valve and thumb pointing downstream in the distal direction. You may also reach across the patient's head, as long as your thumb points distally. If you are the patient performing this on yourself, use the hand on the same side of your body as the shunt. Again, make sure your thumb points distally.

Checking/Flushing CSF Flow in the Proximal Direction (FIGS. 10/12):

With your hand in the proper position, feel the shunt reservoir dome with your middle finger. Your index finger should be over the distal side of the shunt. Carefully press down on the distal occluder with your index finger "as though you were squashing a bug," and hold it depressed while gently depressing and releasing the reservoir using an isolated finger motion. Depressing the reservoir dome without pinching off the occluder will not allow an accurate reading of proximal resistance. Repeat this several times and note its firmness and resilience. Record the reservoir findings on the work page of FIG. 3 under "Proximal" by circling the value that best describes your finding. Be sure to fill in the appropriate sample number.

To flush the shunt valve proximally, completely depress (do not force) the reservoir with your middle finger while the above-noted occluder is pinched off, and then release both fingers. Scoring: −2=very soft feels empty, may or may not refill properly into the reservoir; −1=softer than normal, very fluid, may refill properly; N=Normal function and feel; +1=rather firm, fuller than normal, increased resistance to depressing, may refill slowly, normally or briskly; +2=very firm, may not be able to depress down, refills slowly or briskly.

Figure 9:
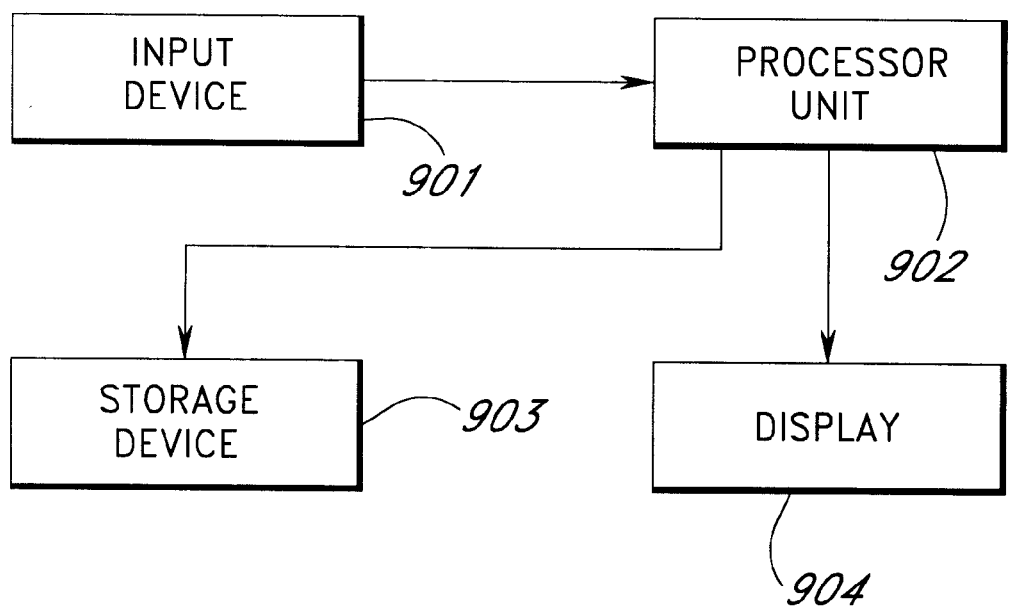
FIG. 9 is an illustration of the components of an apparatus to perform the method of the present invention.

Checking/Flushing CSF Flow in the Distal Direction: (FIGS. 9/11)

With your hand in the proper position, feel the shunt reservoir dome with your middle finger. Next, slide this middle finger over on to the proximal (upstream) side of the shunt. Your index finger should now be directly over the reservoir dome. Press down on the proximal occluder with your middle finger "as though you were squashing a bug," and hold it depressed while very gently depressing and releasing the reservoir, using an isolated finger motion. Repeat several times and note its firmness and resilience. Identify its refill qualities. Record your findings under "Distal," and "Refill," respectively, by circling the values that best describes your findings. Be sure to fill in the appropriate sample number.

To flush the shunt valve distally, completely depress (do not force) the reservoir with your index finger, while the above-noted occluder is pinched off, and then release both fingers. Distal Scoring is the same as Proximal Assessment.

Refill Scoring: −2=very slow to unable to refill; −1=slow to refill, but does so within a couple seconds; N=normal; +1=refills briskly, fuller and faster than normal; +2=refills very quickly, reservoir likely very firm and difficult to depress.

Type 2 Method (In-Line flushing reservoir) (FIGS. 10/12):

Shunt valves that do not incorporate an integral shunt valve with a central reservoir and directional occluders will normally have an in-line flushing reservoir proximal to the valve. Such systems do not permit directional flushing. This technique may be used with Type 1 systems as well, though the results are not as thorough.

To perform the In-Line reservoir test, locate the flushing reservoir with your middle or index finger and position your other fingers comfortably around the reservoir dome. Very gently depress down on the reservoir using an isolated finger motion, and note its firmness. Repeat this motion several times, allowing pauses in between and noting its refill qualities. Record your reservoir findings under "In-line," and "Refill," respectively, on the System work page. Be sure to circle the appropriate sample values. In-Line Scoring: −2=very soft, feels empty of fluid, may or may not refill properly; −1=softer than normal, very fluid, may depress and refill properly; N=Normal function and feel; +1=rather firm, harder than normal, increased resistance to depressing, may refill slowly, normally or briskly; +2=very firm, hard to depress, refills slowly, normally or briskly. Refill Scoring: −2=very slow to no refill; −1=slow to refill within seconds; N=normal; +1=refills briskly, fuller and faster than normal; +2=refills very quickly, reservoir likely very firm.

Step 4. Performing the Cognitive Test. The user selects a cognitive test for the test profile during initial setup. Suggested tests are listed below. The system will now prompt the user to perform a cognitive test. The cognitive tests below are some of the examples of test that can be used to gauge the memory and IQ functions of the tested patient. The results should be based on what is considered normal or below normal for that patient. The user is encouraged to try several different tests. After identifying the cognitive state, circle the score number under "Cognitive" that best describes your findings. Generally, cognitive changes cause an individual to become quiet. Scoring: −3=most severe, unable to talk or express ideas, stare, unable to perform any cognitive tests; −2=moderately severe, quiet, unable to find the right words or be aware of what's happening around them, poor performance on cognitive tests, very irritable, may have a stare; −1=mild deficit, less active, some speaking or memory difficulties, may initially think he/she is OK, yet cognitive tests will be impaired; N=normal or good (for that patient). Typical Scoring for Ages 10 and Over: 5/5 (channels, objects, Words)=N; 4/5=N; 3/5=−1; 2/5=−1 to −2; 1/5=−2; and 0/5=−3.

Suggested Cognitive Tests:

a) TV Multiple Channel Test. Using a TV remote control (if available), have the patient browse a number of channels. From these, pick 5 shows and watch each one for 15 to 30 seconds. Then, allow several minutes to pass and ask the patient to identify the five programs, and corresponding channels if able. You may also query the patient after a longer time interval. Compare the test result to the patient's normal finding and equate it in terms of a score from N to −3 and mark the score on the work page of FIG. 3. Score it according to age and development.

b) Objects Recall. This test can be performed anywhere, even on oneself Identify five or more objects within a room or setting. Use more objects for higher developed patients. Allow several minutes to elapse and ask the patient to recall the objects. Compare this to the patient's pre-established normal function, and equate it in terms of a score from N to −3.

c) Spelling/Phone Numbers. Ask the patient to spell or recall spelling words that he/she would ordinarily know. Start with easier words and go to more difficult words. Choose up to ten words or phone numbers. Compare this to the patient's pre-established or normal function, and equate it in terms of a score from N to −3.

d) Counting Backwards. This test can be started from the numbers 100, 50, 1000, etc.. The objective is to have the patient count backwards. Having the patient count backwards and subtract by 3, 7 or a similar number may increase the level of difficulty. The difficulty level can also be adjusted to age and level of the patient by altering the complexity of the numbers, and by timing of the interval. Compare your findings to the patient's pre-established normal, and equate it in terms of a score from N to −3.

e) Equipment/Game Operation. Pick one of several games or pieces of equipment around the home or office that the patient knows how to operate. Have the patient demonstrate the game or equipment operation. This tests concentration and recall. Suggested tests include computer programs, popular games, televisions, VCRs, etc.. Compare this to the patient's normal or pre-established function, and equate it in terms of a score from N to −3.

Step 5. Performing the Positional Test. Make sure you have first recorded the Nausea, Cognitive, and Headache data on the work page. The patient should already be in a Supine (flat on back) or near Supine position. Next, place the patient in the opposite postural position for 1 to 3 minutes, or until he/she notes a change in the described complaints. Circle a score on the work page according to the scoring below.

Opposite postural positions include a change from lying flat to sitting or standing, standing to lying at a 30-degree upright angle, and a 30-degree upright angle to the Trendelenburg (30-degree head downward) position. If the patient experiences any intolerable worsening of his/her complaints, abandon the posture. Scoring: N (for No Complaints), ↓ for Worsening Complaints, NC for No Change in Complaints, or ↑ for Improving Complaints, under the respective "Supine" or "Upright" column corresponding to the posture. An N score would specify a patient without complaints. An NC score would specify an indeterminate result unchanged by posture.

Next, place the patient in the opposite posture and maintain that for 1 to 3 minutes, or until a change is noted in the described complaints. Circle either N, ↑, NC, or ↓ under the respective "Supine" or "Upright" column. Be sure to circle the appropriate sample.

In the event a NC (indeterminate) score is found, the user may elect to do either of the following: 1) Allow up to ten minutes of time to elapse in the measured postures; or 2) Use the Trendelenburg position (30-degree head down) in place of the Supine position.

The scientific merit in the Positional Test follows that ICP will be higher when lying down, and lower when upright. In shunt malfunction cases where there is increased ICP, the patient should feel worse lying down, and improved when upright. Conversely, in low ICP malfunctions such as overdrainage, the patient would feel improved lying down, and worse when upright. Headache (HA) is the most common outward barometer of ICP change, and widely used in hydrocephalus assessment. Nevertheless, some patients will exhibit nausea, vomiting, or cognitive change more readily than headache.

In addition to the parameters mentioned above other conditions can be observed. Some of those additional conditions are eye signs, balance, proximal refill, and distal refill.

The data gathered by the user is stored in a journal in addition to being passed on to the processing module. Recording the data in a journal allows the system to later use the raw unprocessed data in graphs and more advanced diagnosis tools such the pattern recognition logic discussed below. The user can additionally review the sample data and modify measurements that are erroneous.

DiaCeph™ Processing:

The following description relates to the processing of the sampled values to produce a set of predictions or evaluations. The processor disclosed is a slide ruler processor using tables and forms. The DiaCeph™ Slide Chart Processor allows for analyzing the work page data, determining ICP, and plotting the ICP results on a Day-Chart. The processor employs an "algorithm" relationship to the data. All possible "what if" scenarios are matched. Future additions or changes can be done simply by changing the Answer Cards. The exact relations of the sample data to a diagnosis can be determined in several manners. One possibility is to conduct clinical trails during which patients are observed and diagnosed by invasive methods such as those used in hospital monitoring. Another manner by which the correlation of sample data to the diagnosis can be accomplished is setting a single standard predefined correlation. The diagnosis can be a deviation from that standard correlation resulting from an averaging of the first few samples. In this second method a normalized result is first achieved and the sampling is later used to determine whether the shunt is deviating from normal performance. The computerized version of the processor will incorporate the correlation file and automatically generate a diagnosis based on sample data.

TEMPLATE ONE (FIG. 5)

Step 1. Positional Value Key Column:

Positional Value is a middle equation value for analyzing +, −, N, or /N (indeterminate) postural changes in the Positional Test. Locate the work page insert (FIG. 3). Find the Positional Value data column on the lower left-hand side of the work page. It lists four (4) possible Values, −, +, N, /N. Find the Positional Value Key in the upper left-hand corner of Template One. Read the Positional Value by matching the Positional Test results of the sample to one of the six (6) lines in the Key. Circle the Positional Value result for the sample under Positional Value on the work page (lower left).

Step 2. Determining ICP Value:

ICP, or intracranial pressure, is very important in determining the nature of a shunt malfunction. The normal medical practice for determining ICP is with a direct needle manometer reading through the shunt reservoir, which carries some risk. CT and MRI evaluation of ventricular size is most routinely used to measure a change in ICP, yet is an indirect sampling method.

To determine ICP, Set the Slide Chart in Window (A) to the Cognitive and Headache scores from the work page. Align them with each other on the slide, and then read the resulting ICP Value directly below the patient's Nausea score in either Window (B), (C), (D), or (E), depending on the Positional Value reading from Step 1. Circle this ICP Value under the ICP Value column on the work page.

The ICP processor function is scientifically based on the inter-relationship between nausea, headache, and cognitive changes which follows ICP change. In the shunted patient, adverse ICP changes are brought on by a malfunctioning or improperly matched shunt system, or by changes in the patient's posture. In the DiaCeph™ ICP processor, for example, the more severe the headache in association with a supine postural position, and accompanied by nausea and/or cognitive change, the higher the approximate ICP Value. Due to the methodology in obtaining this non-invasive data, there is a small "indeterminate" area in the /N range where ICP change is either too subtle to register, or is masked by other occurring pathology. To help offset these possible errors, the ICP value is matched with the patient's Shunt System Analysis in Template Three, and inconsistent values tend to be isolated. Additionally the barometric pressure can be measured to further refine the ICP estimate thereby preventing barometric pressure variations from altering the estimate.

Figure 13:
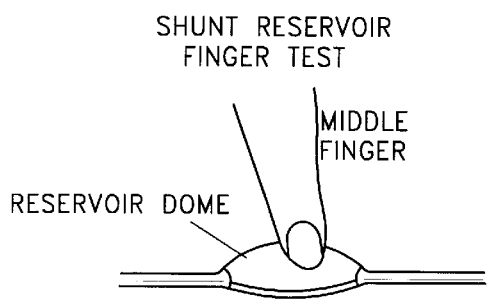
FIG. 13 is an illustration of the shunt reservoir finger testing procedure for the shunt of FIG. 11.

TEMPLATE TWO (FIG. 6):

Step 3. Reservoir Finger Test Analysis:

This step evaluates the Shunt Reservoir Finger Test data. The template provides results in "Letter Coding" of commonly found conditions and Types of Shunt Malfunction (FIG. 13). Locate the Reservoir Test scores for the sample and Set the slide so that the Distal score is aligned with the set the Refill score at the In-Line score.

Step 4. Refill Score:

In Window (G), and without moving the slide, identify the Refill score for the sample in the left-hand column in the box (Type 1 Systems). Read the Coded Answer or match that appears in the window on the same line. Write the Letter Codes in the spaces provided on the work page under the Reservoir Analysis column. For In-Line reservoir test data (Type 2), read the Coded Answer in the window on the line next to "In-Line."

Step 5. Shunt System Analysis:

In Window (H), Set the slide so that the Malfunctions grouping from Step 4 appears in the window. Identify the Shunt Tract finding from the work page in the Box adjacent to Window (I). Read the Coded Answer on that line which appears in the window. Write the Letter Codes in the space on the work page under Shunt System Analysis.

TEMPLATE THREE (FIG. 7):

Step 6. Determining the DiaCeph™ Diagnosis:

Steps 6 and 7 match the patient's ICP Value determined in Step 2 with the Shunt System Analysis just concluded. The results are provided in Letter Codes. In Window (J), Set the Slide Chart so that the arrow above the window is aligned with the Shunt System Analysis Code result from Step 5.

Step 7. Diagnosis:

In Window (K), and without moving the slide, identify the ICP Value from Step 2 in the Box to the left of the window. Read the DiaCeph™ Diagnosis match in the window on the line adjacent to the ICP Value. Circle the Letter Codes on the Key provided on the work page under DiaCeph™ Diagnosis.

The Standard DiaCeph™ Diagnosis is reached by matching the patient's Shunt Reservoir Finger Test results and Shunt Tract exam (Steps 3, 4, 5) to their approximated ICP Value. DiaCeph™ exposes the data to a large field of shunt conditions and malfunctions (Steps 6 and 7). The concept is based on the fact that each shunt malfunction displays a unique set of findings in the DiaCeph™ Test. When these are tracked, scored, and analyzed, they can be matched with specific shunt malfunctions. Once the processing step is complete the user may be prompted to either end the testing, return to the main menu, continue to the advanced portion of the test including interventions, or perform another set of tests to gather an additional sample.

In another embodiment, the processing of values observed can be made dependent on past values by modifying the processing of sampled values in the DiaCeph™ processor. For example the method by which ICP pressure is estimated can vary in accordance with the previous two ICP evaluations. If the previous two evaluations showed an increase in ICP over time, the processing to estimate the next ICP may account for that trend by increasing the weight given to the Nausea score in the processing.

Additionally outside conditions may influence the observations. By measuring conditions such as room temperature and barometric pressure, the processing can be more accurate. Therefore, the DiaCeph™ processor may also include an entry for the temperature and barometric pressure.

Figure 4:
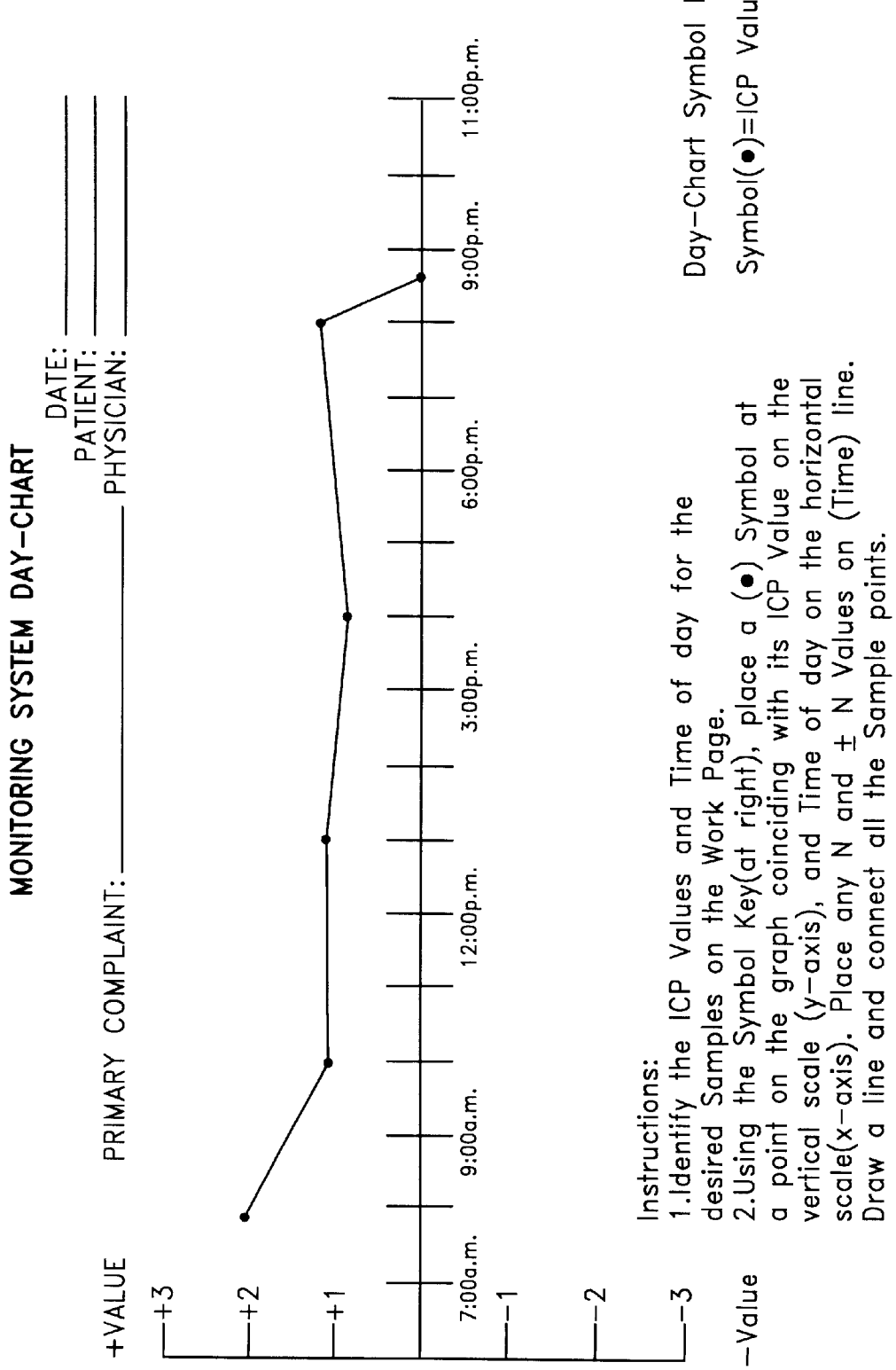
FIG. 4 is an example of a chart tracking shunt performance over the course of one day.

DiaCeph™ ICP Day-Chart (FIG. 4)

The Day-Chart plots the data, for example ICP Values determined from DiaCeph's analysis of the patient's Nausea, Headache, Cognitive, and Positional Value scores, as a function of time. The data for plotting is taken from the journal. For example the resulting graph of FIG. 4 provides a display of the patient's rising and falling ICP as he/she undertakes various activities. By comparing an incident graph to the patient's normal, even the most episodic shunt malfunction becomes clearer. The normals for each graph will vary according to the type of shunt system and hydrocephalus pathology. Each patient should pre-establish a normal Day-Chart so as to permit informative comparison to an incident graph.

The graph of, for example, the ICP values may be compared to a predefined set of deviations from a normal values for a specific incident or malfunction. DiaCeph™ can include a processor to correlate a predefined sets of deviations, relating to a specific incident, to the current set of measurements. This correlation can be accomplished by, for example, storing a ten value set for each incident The last ten observations of a patient can be compared to the multiple sets of values by calculating the aggregate difference between the elements of the current set with the elements of the stored sets. The stored set for which the aggregate difference is the least is the closest to the current set. Therefore the processor will generate the diagnosis as the incident for which the set closest to the current set. The comparison to the predefined sets can be done for each observed condition data or for the entire set of observed conditions.

As a stand-alone single observed condition, for example ICP value, the comparison would follow the steps outlined above. The diagnosis can be made more accurate at times, if more than one measured condition data is correlated to a predefined set. For example, a set of data over time, in the form of values such as ICP, reservoir analysis score, refill score, can be stored for a given incident. The data from a sample of those same observable conditions can be compared to the sets of values for a given incident by following the same procedure outlined above for the single data set. A correlation will be concluded if the aggregate differences between the observed set and an incident data is less than that for the other incidents. In this manner more than one observable condition is evaluated in determining whether an incident corresponds to a set of measurements over time. A more refined analysis can be made by evaluating the relationship of the stored incident data to more than one observable condition. Alternatively the data can be plotted against time and manually compared to predefined graphs for certain incidents.

Advanced DiaCeph™ Test (Interventions)

DiaCeph™ Interventions are an advanced segment of the DiaCeph™ Test. They entail shunt system manipulations that both isolate a specific shunt malfunction and/or help treat its associated complaints. In certain cases, these Interventions can be used to remedy an ensuing shunt malfunction. However, due to their nature and under certain circumstances, a neurosurgeon may advise against a specific DiaCeph™ Intervention because of a possible risk of aggravating an ensuing malfunction. There is some risk the Intervention could exacerbate the failing or disconnected component. To address this issue, the Slide Chart processor provides a "not recommended" key code in window (M) of template three. When used according to the instructions, DiaCeph™ Interventions are safe and effective to the shunted patient.

TEMPLATE THREE (FIG. 7):

Step 8. Determining the Interventions:

This step correlates specific Interventions, determined by the DiaCeph™ processor, in assessing the complex hydrocephalus patient. A few of the Interventions may be contraindicated under certain circumstances. DiaCeph™ provides a "not recommended" Code Key to alert the user to these occasions.

In Window (L), Set the Slide Chart so that the arrow above the window is aligned with the DiaCeph™ Diagnosis result from Step 7. In Window (M), and without moving the slide, read the Interventions and Malfunctions Codes that appear in the window adjacent to "First Priority, Second Priority," etc. in the box. Write these numbers and letters on the spaces provided on the work page under Interventions.

Step 9. Performing Interventions:

Start with those Interventions marked "First Priority" in Window (M). After performing the Intervention, assess the patient's Status by determining if there has been any change in his/her complaints. Base your assessment on substantive changes in Nausea, Headache, and/or Cognitive complaints. Headache is accepted as the most measurable complaint in hydrocephalus assessment, but it can vary from patient to patient. See also discussion under Positional Testing. Circle your findings under the "Status" column on the work page.

The concept behind DiaCeph™ Interventions (Advanced DiaCeph™ Test) is to non-invasively challenge complicated shunt malfunctions, and reaffirm or reject a diagnosis. The Interventions are manipulations of the patients body posture, his/her ICP pressures, and CNS shunt system. They are designed to result in known specific outcomes that coincide with rising or falling ICP and specific shunt malfunction. The Advanced DiaCeph™ Test has been shown to remedy some common shunt complaints. It serves to assist the neurosurgeon in determining subsequent clinical testing and/or surgery.

On Template Three of the Slide Chart, in Window (L), there are Malfunction Codes and groups displayed across the middle section of the answer card, which are based on the possible matches in Step 7, Window (K). Beneath this window, in Window (M), are columns of the Malfunction Code/groups, each having rows of matching Interventions and counterpart Letter Codes, and one row of "Not Recommended" Codes. The following interventions are an example of some of the procedures that may be recommended by reference to the malfunction code/group determined by the processing steps:

1. Lay Down and Rest: This simple method is for evaluating low ICP (over-drainage) versus increased ICP (under-drainage). Place the patient flat (supine) for a period of several minutes to 15 minutes. A low ICP state would find a noticeable improvement. An elevated ICP state would find a worsening of the complaints lying down. Other pathological conditions could improve with rest, though unlikely improvement would occur immediately.

2. Lay Down to Trendelenburg: This position is described as laying supine (on one's back) with the head tilted lower than the feet at an approximate thirty degree angle. This position is used for treating and evaluating over-drainage. Lay in this position for 1 to 3 minutes. Typically, either improvement or worsening will be seen almost immediately, and the position can be abandoned.

3. Exercise Activities: Exercise both raises a person's ICP, and causes increased blood flow to the brain. In some cases, staining and increasing ICP can improve CSF flow in a sluggish shunt system. It can, however, be harmful to a person with elevated ICP, as ICP will further increase. In cases of over-drainage, exercise can purge and refresh stagnant venous blood flow caused by dilated vessels reacting to chronic over-drainage. Exercise has an additional positive hormonal effect upon the brain by stimulating the release of endorphins and related chemicals that act to minimize pain and boost a feeling of well-being.

4. Pinch off Shunt Occluder: Requires shunt valve with proximal or distal occluder. Have the patient assume a comfortable sitting or standing position. Pinch off an occluder port with steady finger pressure and hold for 1 to 3 minutes. Record the change in complaints. Over-drainage would reveal an improved level of complaints. Under-drainage would reveal no change, or a worsening level of complaints.

5. Close ASD Device: Occasionally, an ASD (anti-siphon device) mechanism will fail to retard CSF fluid in the upright posture, leaving the patient over-draining with an otherwise lower pressure shunt. This Intervention requires the user to pinch off the proximal occluder and depress the reservoir, hold the occluder pinched for 1 to 2 minutes. Alternatively, flush the shunt proximally several times.

6. Assume an Upright Posture: This is effective in isolating whether complaints are due to shunt over-drainage or under-drainage. It also brings relief to the latter condition. Under-drainage may be related to a number of malfunction processes. Sit up or stand for 3 to 10 minutes, and observe any change in condition.

7. Flush Distally/Strain/Purge: Selective flushing can only be performed on a shunt with central reservoir and proximal and distal occluders. An in-line reservoir system normally flushes distally. In the event of a distal obstruction, flushing may cause CSF fluid to flow proximally. Refer to the "flushing instructions" under the Shunt Reservoir Finger Test. To flush, lay down in a supine up to a 30 degree position and perform 2 to 3 proximal flushes, followed by the same number of distal flushes. Repeat several times if desired. To purge, slowly tense up the body, hold and relax. Flush the shunt valve during relaxation. To use straining to assess ICP, lay supine to a 30 degree angle and bear down (tense up) slowly and hold for several seconds, and relax and repeat. If ICP is already elevated, straining will be uncomfortable and often not possible. If ICP is low, straining brings relief. Staining increases ICP and blood flow within the brain and can be harmful in cases of elevated ICP.

8. Lift Up Overlying Scalp: In a supine, 30 degree or sitting position, reach with the fingers of either hand to a spot 1 to 2 inches below the shunt and push up on the scalp so as to create a loose (flap) pocket of scalp around the shunt. Hold this for 1 to 3 minutes. This test isolates overlying scalp pressure as a cause of upright ASD shunt over-function.

9. Flush Valve Proximally: This requires a patient with a shunt with central reservoir and proximal and distal occluders. Refer to flushing instructions under the Shunt Reservoir Finger Test. It is best to lie in a reclined position. Pinch off the distal occluder, and depress the reservoir with several finger depressions.

10. Manipulate Abdomen/Shunt Tract: A disconnected component, or a mal-positioned peritoneal catheter, can prevent the required CSF flow from reaching its destination. Gently manipulate each suspect area to effect a change in CSF flow through the shunt system. An improving or worsening level of complaints following this would suggest it is the cause of the shunt malfunction. In the case of a mal-positioned peritoneal catheter, repositioning may be accomplished by having the patient take a breath as you manipulate the abdomen.

11. Diamox Therapy: Diamox, or acetazolamide, is a specific type of diuretic drug that has been found to reduce the rate of CSF production in the brain, thereby lowering one's ICP. The drop in CSF production, though not of any great amount, has its application the treatment of hydrocephalus. It is commonly prescribed in the initial onset of hydrocephalus, and is used to relieve complaints associated with increased ICP due to intermittent shunt malfunction, and in general cases of insufficient CSF outflow.

Diamox additionally has a diagnostic value. It can be used as an Intervention in the DiaCeph™ test in verifying the presence of increased, normal, or decreased ICP, as it slows CSF production and lowers ICP. The patient should take Diamox according to the times and doses prescribed by their treating physician. An improvement in complaints would be evidence of increased ICP; a no change in complaints would indicate either very elevated ICP and/or other pathology; and a worsening in complaints would indicate either a low ICP condition, a reaction to the Diamox, or too strong a dose.

12. Elastic Wrap Over ASD: Placing an elastic wrap over an ASD shunt would, under normal circumstances, cause the shunt to open at a "higher" opening pressure, effectively reducing CSF outflow. An ASD device is one that has an anti-siphon membrane to prevent over-drainage. When external pressure is applied to the membrane, or a drop in hydrostatic pressure occurs, the flow of fluid is further inhibited. ASD devices base their shunt opening pressure on a sensor below the scalp which is referenced to normal atmospheric pressure. Any increase in scalp pressure over this sensor would cause the device to open at a higher opening pressure, thus elevating ICP.

These effects are very difficult to determine with routine testing. Placing an elastic wrap over the ASD device has diagnostic implications, by causing a patent shunt system to reduce CSF outflow, and measuring the resulting change in the patient's complaints. A worsening of complaints would suggest responsive increase in ICP. A matching of complaints to what was seen in a previous shunt malfunction incident tends to confirm the suspected incident. An improvement in complaints would suggest a low ICP condition, and shunt overdrainage at that time.

Depending on the shunt malfunction that is being explored, this Intervention could be used to mimic complaints caused by sleeping firmly on the shunt, to confirm overlying scalp pressure as a cause of shunt insufficiency, or to cause momentary relief in an ASD implanted patient suspected of overdraining. This procedure should be performed by and only according to the specific protocol of the treating physician.

TEMPLATE FOUR (FIG. 8):

Step 10. Processing the Interventions:

Steps 10 and 11 enable the user to process post Intervention results by aligning the slide arrow up with the Intervention results in Window (N). Window (O) then provides the user with malfunction codes that correspond to a match on the line adjacent to each malfunction. In any given Intervention test, there may be one to several matches.

Since a few of the Interventions pose a small but measurable risk of injury to the shunt system, DiaCeph™ provides a "not recommended" code key also under Window (O) to alert the user to an Intervention that could be contraindicated. The user should also exercise good judgement in determining whether or not to perform a "NR" noted Intervention.

In Window (N), Set the Slide Chart so that the arrow below the window is aligned with the symbol results ↑, NC, or ↓ of the Intervention number being processed.

Step 11. Advanced DiaCeph™ Diagnosis:

In Window (O), and without moving the slide, read the Malfunction Code Letter(s) which appear in the window. Read the Coded results which appear on the same lines as the Malfunctions (listed at left) being evaluated. A Malfunction code appearing in Window (O) represents an affirmative match (diagnosis) with that malfunction, whereas a "−" symbol represents a rejection of that malfunction as a diagnosis. A percent "%" symbol appearing in Window (O) adjacent to the malfunction denotes a possibility that the malfunction exists. Note any "NR" (not recommended) Codes. Post the results to the work page by circling the respective Letter Code(s) under "Advanced Diagnosis."

Continue performing the Interventions specified in Step 8, Window (M), until a single diagnosis has been reached, or all have been completed and the field cannot be further narrowed.

The results from applying the Interventions are based on current scientific understanding of shunt systems, ICP needs and postural changes, and CSF flows.

By assigning various Number and Letter Codes to patient data, shunt conditions, malfunctions, and Slide Chart results, the Advanced DiaCeph™ Test is able to handle as much as 390 possible shunt scenarios.

The procedure for sampling and processing the data can be made dependent on the shunt type observed. Since various shunt types can be used for patients, variations in shunt structure exist. Therefore, the sampling steps of the DiaCeph™ procedure should vary with the shunt type observed. This variation in sampling can be accomplished by, for example, prompting the user to select a shunt type from a menu at the start of testing when the procedure is implemented as a computer program or electronic device. The menu selection of shunt type will then affect the sampling steps of the process by allowing for skipping certain steps and performing others depending on the shunt type selected. In this manner the DiaCeph procedure can be used by patients with various shunt types without requiring the user to know which sampling procedure is relevant to the specific shunt observed.

The DiaCeph™ processor can be implemented as an electronic data processing device. With reference to FIG. 9, the device can be a specially made unit that includes an input device 901, a processor unit 902, a storage device 903, and a display 904. The processor unit 902 may include memory and a signal processing chip. The processing unit 902 may be a personal computer. The input device 901 can be a keyboard or a data port. The storage device 903 may be a hard disk drive or a floppy disk. The display 904 may be any computer display screen. The DiaCeph™ processor, in another alternative, can be wholly implemented as a software program. The program may include a routine to accept input data, a routine to process the data, and a routine to provide the data to some output device such as the computer display monitor. The program may include a database file that is used by the processing routine. The database file may be updated from time to time as the correlation between input data and prediction is further refined.

Although the invention has been described in terms of certain preferred embodiments, other embodiments that are apparent to those of ordinary skill in the art are also within the scope of this invention. Accordingly, the scope of the invention is intended to be defined by the claims that follow.

What is claimed is:

1. A method of determining a probable operating condition of a Central Nervous System (CNS) shunt, said method comprising:

quantifying the nausea level for the patient;

quantifying the headache level for the patient;

quantifying the possible condition of the CNS shunt by conducting a physical examination of the shunt valve, connectors, and distal catheter of the shunt;

quantifying the cognitive state of the patient by performing at least one test;

quantifying the change in complaints for the patient when changing positions from one postural position to another; and processing the results of said quantified measurements by performing the following steps:

determining the positional change value;

estimating intracranial pressure by correlating a value to the results of said cognitive, headache, and nausea quantification;

correlating at least one code for a CNS shunt condition to said possible condition of the CNS shunt; and correlating at least one code, corresponding to a shunt performance prediction, to said estimated intracranial pressure and said code for said CNS shunt condition.

2. The method of claim 1 further comprising the step of recommending an intervention based on said prediction.

3. The method of claim 1 further comprising the steps of:

selecting an intervention based on said shunt performance prediction;

performing said intervention;

assessing the status of the patient by making at least one additional observation; and narrowing a range of predicted CNS shunt operation conditions by using the results of said additional observation.

4. The method of claim 1, further comprising the additional step of storing all predictions for a patient.

5. The method of claim 1 wherein a procedure is repeated until a single predicted CNS shunt operation condition remains, said procedure comprising the steps of:

assessing the status of the patient by making at least one additional observation; and narrowing the range of predicted CNS shunt operation conditions by using the results of said additional observation.

6. The method of claim 1 wherein the step of estimating intracranial pressure includes a barometric pressure measurement.

7. A method of determining a probable operating condition of a Central Nervous System (CNS) shunt, said method comprising the steps of:

estimating the relative intracranial pressure by using a set of non-invasive observations;

conducting an examination of said CNS shunt;

processing the results of said intracranial pressure estimate and said shunt examination to provide at least one prediction of CNS shunt operation condition; and communicating said at least one prediction to a user by selecting a description from a set of prediction descriptions.

8. A method of estimating intracranial pressure changes in a patient having a CNS shunt, said method comprising the steps of:

generating a score for the patient nausea level;

generating a score for the patient headache level;

generating a score for the patient cognitive response level; and correlating said nausea score, said headache score, and said cognitive response score to estimate the said pressure changes.

9. The method of claim 8 further comprising the additional steps of generating a score for eye signs of the patient and correlating the eye sign score to estimate said pressure changes.

10. The method of claim 8 further comprising the additional step of generating a score for balance of the patient and correlating the balance score to estimate said pressure changes.

11. The method of claim 10 further comprising the steps of:
   generating a score for a patient eye signs level;
   generating a score for a patient malaise level; and
   correlating said eye sign score and said malaise score to estimate said pressure changes.

12. The method of claim 8 further comprising the additional step of generating a score for a malaise level of the patient and correlating the malaise level to estimate said pressure changes.

* * * * *